US011266333B2

(12) United States Patent
Foresto (10) Patent No.: US 11,266,333 B2
(45) Date of Patent: Mar. 8, 2022

(54) APPARATUS AND METHODS FOR MONITORING HYPOXIA (71) Applicant: Joseph Foresto, Greenlawn, NY (US)

(72) Inventor: Joseph Foresto, Greenlawn, NY (US)

(*) Notice: Subject to any disclaimer, the term of this patent is extended or adjusted under 35 U.S.C. 154(b) by 152 days.

(21) Appl. No.: 16/393,230

(22) Filed: Apr. 24, 2019

(65) Prior Publication Data
US 2019/0328294 A1 Oct. 31, 2019

Related U.S. Application Data (60) Provisional application No. 62/663,071, filed on Apr. 26, 2018.

(51) Int. Cl.
*A61B 5/1455* (2006.01)
*A61B 5/00* (2006.01)

(52) U.S. Cl.
CPC ........ *A61B 5/14552* (2013.01); *A61B 5/0002* (2013.01); *A61B 5/6824* (2013.01); *A61B 5/6831* (2013.01); *A61B 5/742* (2013.01); *A61B 5/7405* (2013.01); *A61B 5/746* (2013.01); *A61B 5/7455* (2013.01)

(58) Field of Classification Search
CPC .... A61B 5/1455–14557; A61B 5/6824; A61B 5/6831; A61B 5/681; A61B 5/746; A61B 5/0002; A61B 5/7405; A61B 5/002; A61B 5/0022
See application file for complete search history.

(56) References Cited

U.S. PATENT DOCUMENTS

| 10,321,879 | B2 * | 6/2019 | Delia ................... A61B 5/6806 |
| 2012/0238834 | A1 * | 9/2012 | Hornick ............. A61B 5/14542 600/301 |
| 2014/0142403 | A1 | 5/2014 | Brumback et al. |
| 2014/0200423 | A1 | 7/2014 | Eisen et al. |
| 2015/0018647 | A1 * | 1/2015 | Mandel ............. A61B 5/14552 600/323 |
| 2016/0367183 | A1 * | 12/2016 | Miyasaka .............. A61B 5/486 |
| 2017/0172476 | A1 * | 6/2017 | Schilthuizen ........ A61B 5/1455 |
| 2017/0251962 | A1 * | 9/2017 | Shiho .................... A61B 5/681 |

(Continued)

OTHER PUBLICATIONS

McKee et al., "Pulse Oximeter Display System: Project Proposal Feasibility Report", Calvin College, pp. 1-37 (Year: 2014).*

(Continued)

*Primary Examiner* — Eric F Winakur
(74) *Attorney, Agent, or Firm* — Hoffmann & Baron, LLP (57) ABSTRACT An oximetry device for monitoring blood oxygen saturation of a user includes a main body and a wrist strap coupled with the main body and adapted to removably secure the main body on a wrist of the user during operation of the device. The main body includes an oximeter sensor adapted to generate an output signal indicative of measured blood oxygen saturation, a controller in operative communication with the oximeter sensor and configured to determine a percentage blood oxygen saturation of the user as a function of the output signal generated by the oximeter sensor, and a display for presenting visual information generated by the controller to the user. The display includes a changeable backlighting color, the controller being configured to adjust a color of the display backlighting as a function of a measured blood oxygen saturation of the user.

14 Claims, 4 Drawing Sheets (56) References Cited

U.S. PATENT DOCUMENTS

2018/0132794 A1* 5/2018 Lange ................. A61B 5/4035
2018/0368701 A1* 12/2018 Vule .................... A61B 5/0205

OTHER PUBLICATIONS

McKee et al, "Pulse Oximeter Display System: Project Proposal Feasibility Report", 2014, Calvin College, pp. 1-37 (Year: 2014).*
McKee et al., "Pulse Oximeter Display System: Project Proposal Feasibility Report", ENGR 339 Senior Design Project, Calvin College, pp. 1-37; 2014.
http://www.aswechange.com/buy-color-changing-pulse-oximeter-356312; 2019.

* cited by examiner

APPARATUS AND METHODS FOR MONITORING HYPOXIA

CROSS-REFERENCE TO RELATED APPLICATIONS

This application claims the benefit of priority to U.S. Provisional Patent Application No. 62/663,071 filed on Apr. 26, 2018 and entitled "Physiological Altitude Indicator," the disclosure of which is incorporated by reference herein in its entirety for all purposes.

FIELD

The present invention relates generally to the electrical, electronic and computer arts, and, more particularly, to techniques for monitoring hypoxia.

BACKGROUND

Oxygen in the ambient air must ultimately reach the cells of the body, and it does so because of a number of factors, including gas laws, the lungs, circulatory system, blood and hemoglobin. An interruption affecting any one of these factors can result in hypoxia. For instance, ambient atmospheric partial pressure of oxygen decreases with increasing altitude (i.e., ascent), which translates into a lower pressure gradient in the lungs for diffusion to occur in the alveolar membrane (Dalton's and Graham's gas laws). Hemoglobin (Hgb), a primary transporter of oxygen in the blood, does not have access to adequate amounts of oxygen to attach, or there isn't sufficient hemoglobin available. Oxygen molecules are biochemically attached to the hemoglobin molecule, which is affected by the surrounding partial pressure of oxygen (and carbon dioxide), which in turn transfers these gases to and from the tissue cells. The oxygen-hemoglobin dissociation curve indicates a rapid decrease of saturation, and transfer, when oxygen partial pressure drops below about 60 millimeters of mercury (mmHg). Ideally, arterial pressure should be near 80-90 mmHg, or a saturation of 87-97 percent.

Hypoxia is a condition in which the body or a region of the body is deprived of adequate oxygen supply at the tissue level. Hypoxia may be classified as either generalized, affecting the whole body, or local, affecting a region of the body. Generalized hypoxia occurs in healthy people when they ascend to high altitudes, where the condition is often manifested as altitude sickness leading to potentially fatal complications, including, for example, high altitude pulmonary edema (HAPE) and high altitude cerebral edema (HACE). Certain activities, such as, for example, flying or mountain climbing, can place an individual at risk for hypoxia.

Because nervous system tissues are perhaps most critically affected by a lack of oxygen, especially the brain and eyes, most hypoxic symptoms are directly or indirectly related to the nervous system. If hypoxia is prolonged, serious impairment, and ultimately death, will occur. One of the most dangerous characteristics of hypoxia is that if the individual is hypoxic and engrossed in an activity (e.g., flight duties, etc.), the individual might not even be aware of the impairment. Because hypoxia often develops gradually, a person must recognize its various stages, allowing some degree of anticipation if symptoms are identified in the early stages. The earlier that hypoxia can be recognized, the sooner that corrective action can be taken before the individual becomes unable to act appropriately.

One technique for monitoring certain physiological characteristics of a person is commonly referred to as pulse oximetry, and devices based on pulse oximetry techniques are referred to as pulse oximeters. Standard pulse oximeters are typically attached to the finger of a patient (e.g., clipped to the tip of the finger) and are used to non-invasively measure arterial blood oxygen saturation of hemoglobin, and/or the rate of blood pulsations corresponding to each heartbeat of the patient. One disadvantage of a standard pulse oximeter, however, is that its placement on the finger of an individual significantly hampers an ability of the individual to engage in certain activities, particularly those that require full manual dexterity, such as, for example, flying a plane or rock/mountain climbing. Although there are pulse oximeters adapted to be worn on the wrist of a user (see, e.g., U.S. Patent Application Publication No. 2014/0200423 to Eisen et al.), such devices generally require the user to scroll through and select various menu options, etc., or otherwise do not provide a clear and ready indication of blood oxygen saturation levels.

SUMMARY

The present invention, in one or more embodiments thereof, includes apparatus, methods and/or systems for facilitating the monitoring of hypoxia. Specifically, aspects of the invention beneficially provide a wearable apparatus for monitoring hypoxia in a user without impeding the user's ability to engage in tasks requiring full manual dexterity, such as, for example, flying a plane, mountain climbing, etc. One or more embodiments of the invention are manifested in a device adapted to be worn on the wrist of the user and which includes a display which changes color to advantageously provide a clear indication of the stages of hypoxia related to the user's arterial blood oxygen saturation levels.

In accordance with one embodiment, an oximetry device for monitoring blood oxygen saturation of a user includes a main body and a wrist strap coupled with the main body and adapted to removably secure the main body on a wrist of the user during operation of the device. The main body includes an oximeter sensor adapted to generate an output signal indicative of measured blood oxygen saturation, a controller in operative communication with the oximeter sensor and configured to determine a percentage blood oxygen saturation of the user as a function of the output signal generated by the oximeter sensor, and a display for presenting visual information generated by the controller to the user. The display includes a changeable backlighting color, the controller being configured to adjust a color of the display backlighting as a function of a measured blood oxygen saturation of the user accompanied by both a tactile, e.g., vibration and audible alarm to bring attention to the evolving potential of hypoxia.

Optionally, the main body further comprises a wireless interface in operative communication with the controller, the interface being configured, in a group protection mode of operation, to communicate with at least a second oximetry device. A controller in the second oximetry device is adapted to receive an alert signal from the oximetry device when the blood oxygen saturation of the user of the oximetry device falls below a prescribed threshold level and to present an alert indication to a user of the second oximetry device.

As may be used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a non-transitory computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques according to embodiments of the present invention can provide substantial beneficial technical effects. By way of example only and without limitation, one or more embodiments of the invention provide techniques for monitoring hypoxia having one or more of the following advantages, among other benefits:

- wearable on a user in a manner which allows the user unimpeded use of his or her hands, particularly for activities requiring full manual dexterity
- provides a color-changing display for quickly and passively (i.e., without user action) indicating the stages of hypoxia in the user
- provides multiple modes of hypoxia alert indication, including visual, audible and tactile
- capable of establishing a local area network with other oximeter devices, whereby interconnected oximeter devices are configured to perform redundant hypoxia monitoring of all members in a group protection mode of operation
- provides user position information, including altitude, for a more accurate determination of the state of hypoxia in the user
- capable of storing historical physiological information relating to the user and transferring such information (wired or wirelessly) to another system, such as a black box recording device or a pilot's electronic flight bag These and other features and advantages of the present invention will become apparent from the following detailed description of illustrative embodiments thereof, which is to be read in connection with the accompanying drawings.

BRIEF DESCRIPTION OF THE DRAWINGS, (WHICH MAY BE MODIFIED AS PRODUCTION PROGRESSES)

The following drawings are presented by way of example only and without limitation, wherein like reference numerals (when used) indicate corresponding elements throughout the several views, and wherein.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present invention will be described herein in the context of an illustrative wearable fashionable apparatus, methods and/or systems for monitoring hypoxia so that the status of blood oxygen saturation level of a user is clearly indicated to the user and in such a manner as to allow the user unimpeded use of his or her hands, particularly for activities requiring full manual dexterity. It is to be appreciated, however, that the invention is not limited to the specific apparatus, methods and system illustratively shown and described herein. Rather, it will become apparent to those skilled in the art given the teachings herein that numerous modifications can be made to the embodiments shown that are within the scope of the claimed invention. That is, no limitations with respect to the embodiments shown and described herein are intended or should be inferred.

As previously stated, one disadvantage of standard pulse oximeters adapted to be placed on the finger of a user is that it significantly impedes the ability of the user to engage in certain activities such as, for example, flying a plane, rocking climbing, or other activities requiring full manual dexterity. Although there are some known pulse oximeters adapted to be worn on the wrist of a user, such devices generally require the user to scroll through and select various menu items, which again significantly interfere with tasks requiring the use of the user's fingers. Additionally, known devices worn on the wrist of the user do not provide a clear and ready indication of blood oxygen saturation levels sufficient to be able to quickly and easily discern whether immediate corrective action is required.

Aspects of the present invention beneficially provide a wearable apparatus for monitoring hypoxia in a user without impeding the user's ability to engage in tasks requiring full manual dexterity, such as, for example, flying a plane, mountain climbing, etc. An oximeter device according to embodiments of the invention finds beneficial use for individuals engaged in high-altitude activities, including pilots, alpine backpackers and rock climbers, for individuals living in high altitude regions of the world, and for individuals with physical issues that reduce their ability to extract oxygen (e.g., persons suffering from emphysema, chronic obstructive pulmonary disease (COPD), lung cancer, etc.). One or more embodiments of the invention are manifested in a device adapted to be worn on the wrist of the user and which includes a display which changes color to advantageously provide a clear indication of the stages of hypoxia related to the user's arterial blood oxygen saturation levels.

By way of example only and without limitation, in one or more embodiments a display of the hypoxia monitoring device according to aspects of the invention is configured to provide a first color of backlighting, preferably green, to indicate that the user's blood oxygen saturation level is within a prescribed normal range with a low limit of normal functioning to the highest percentage (e.g., about 93%-100%) necessary to sustain routine bodily functioning. When the blood oxygen saturation level of the user falls below a prescribed minimum threshold necessary to sustain routine bodily functioning but is still above a critical threshold level sufficient for sustaining necessary bodily functioning (e.g., about 80%-92%), the display backlighting changes to a second color, preferably yellow or orange, indicating an onset of hypoxia and cautioning the user should take corrective action to avoid becoming hypoxic. When the user's blood oxygen saturation level falls below the critical threshold level for sustaining necessary bodily functioning (e.g., less than about 80%), the display backlighting changes to a third color, preferably red, indicative of an alarm condition signaling impairment of critical bodily functioning. It is to be appreciated that the specific colors and/or the number of different colors used to indicate the particular stages of hypoxia of a user are not limited by embodiments of the invention.

Figure 1:
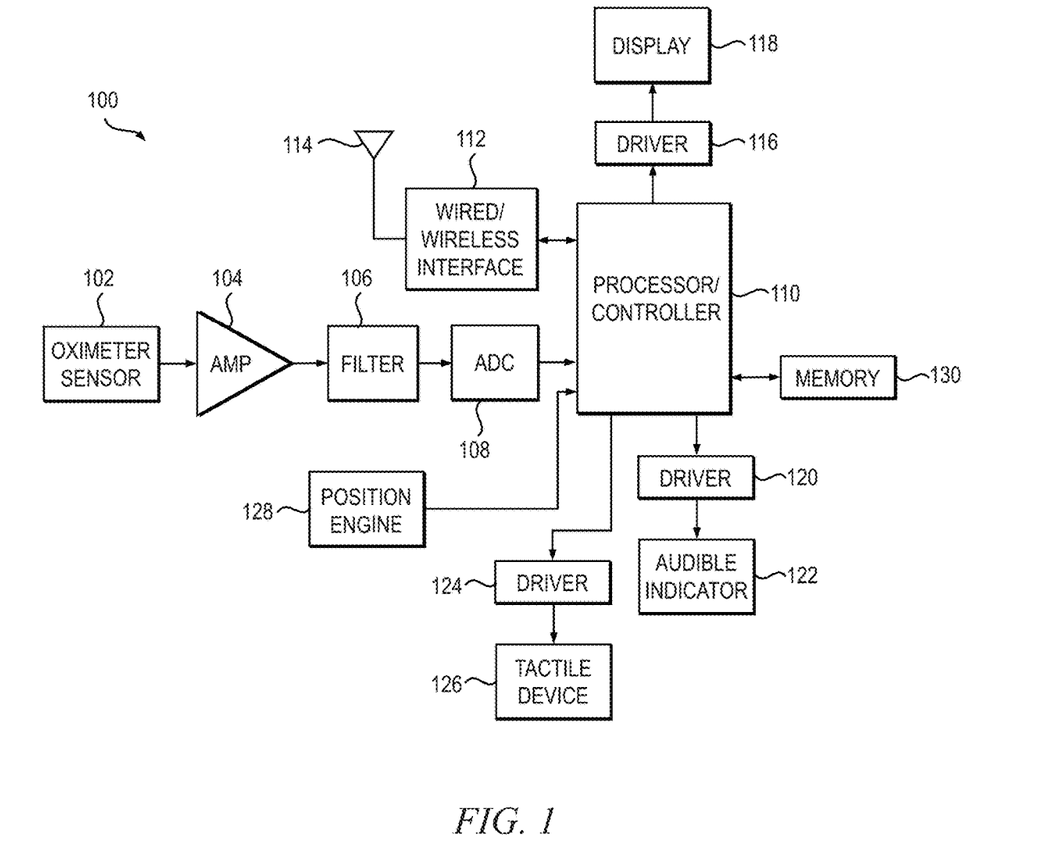
FIG. 1 is a block diagram depicting at least a portion of an exemplary apparatus for monitoring hypoxia stages of a user, according to an embodiment of the present invention.

FIG. 1 is a block diagram depicting at least a portion of an exemplary apparatus 100 for monitoring hypoxia stages of a user, according to an embodiment of the invention. The apparatus 100 includes an oximeter sensor 102 for measuring blood oxygen saturation of the user. Although not explicitly shown, the oximeter sensor 102, in one or more embodiments, preferably includes a light source (e.g., light-emitting diode (LED) or the like) and a light detector (e.g., photodiode, phototransistor, or similar), with the light detector being disposed in alignment with the light source so that the light source passes through an artery of the user and the light not absorbed by oxygen-saturated hemoglobin in the blood is received by the light detector. The light is partly absorbed by hemoglobin by amounts which differ depending on whether the hemoglobin is saturated or desaturated with oxygen.

A typical pulse oximeter uses an electronic processor and a pair of small light-emitting diodes (LEDs) facing a photodiode through a translucent part of the patient's body, such as a fingertip, an earlobe, or a wrist. One LED is red, with wavelength of 660 nm, and the other is infrared with a wavelength of 940 nm. Absorption of light at these wavelengths differs significantly between blood loaded with oxygen and blood lacking oxygen. Oxygenated hemoglobin absorbs more infrared light and allows more red light to pass through. Deoxygenated hemoglobin allows more infrared light to pass through and absorbs more red light. For example, an output signal generated by the oximeter sensor 102 will be indicative of the amount of light absorption, which directly correlates to the amount of oxygen-saturated hemoglobin in the blood. When the output signal of the oximeter sensor 102 is a low level, this is generally indicative of a high light absorption and therefore high oxygen saturation level in the blood. Similarly, when the output signal from the oximeter sensor is a high level, this is generally indicative of low light absorption and therefore low oxygen saturation level in the blood.

In one or more embodiments, the oximeter sensor 102 is disposed on the apparatus so that at least a portion of the wrist of the user passes between the light source and the light detector, or in some other manner which allows the oximeter sensor to non-invasively obtain a measure of the blood oxygen saturation level of the user. For example, in one or more embodiments, the light source of the oximeter sensor 102 may be affixed to the apparatus so that it is in contact with a top (i.e., upper) surface of the skin of the wrist, and the light detector of the oximeter sensor may be affixed to the apparatus so that it is in contact with under a side of the wrist, or vice versa.

The output signal generated by the oximeter sensor 102 is generally a very low level signal and may include an undesirable noise component, and therefore this output signal is preferably amplified to an appropriate level so that subsequent signal processing can be performed. Specifically, in one or more embodiments, the output signal generated by the oximeter sensor 102 is presented to an input of an amplifier 104 (e.g., an operational amplifier or other differential, low noise amplifier). A gain of the amplifier 104 is preferably set to a prescribed value that meets signal level requirements for a subsequent processing stage. The amplifier 104 may also buffer the oximeter sensor 102 from impedance loading effects introduced by circuitry coupled to the output of the sensor. In one or more embodiments, a multiple-stage amplifier is employed (e.g., a voltage amplification stage and an output stage), although the use of single-stage amplifier topologies is similarly contemplated.

An amplified oximeter sensor signal generated by the amplifier 104 is, in one or more embodiments, presented to a filter 106 configured to remove or reduce unwanted noise components from the oximeter sensor signal. For instance, the filter 106 may comprise an active and/or passive low-pass filter network and may include a single stage or multiple filter stages. An analog filtered sensor signal generated as an output of the filter 106 is converted to a corresponding digital signal by passing the filtered sensor signal through an analog-to-digital converter (ADC) 108. The ADC 108 is configured to receive the analog filtered sensor signal as an input and to convert it to a discrete-time digital signal indicative of the analog filtered sensor signal. Characteristics of the ADC 108, including, but not limited to, resolution, sampling frequency, bandwidth, etc., are preferably selected to meet prescribed criteria of the analog filtered sensor signal presented to the ADC.

The digital signal generated by the ADC 108 is presented to a processor or other controller 110. The controller 110, in one or more embodiments, is configured to perform all necessary processing of the oximetry data generated by the oximeter sensor 102 in order to determine the blood oxygen saturation level of the user, to monitor and display a status of the user's blood oxygen saturation level, and to generate alerts when the blood oxygen saturation level of the user falls below a prescribed threshold warranting corrective action, among other functions and features performed by the controller. The controller 110 is configured to run software code which, when executed by the controller, causes the controller to implement one or more of its functions. In this manner, the controller 110, by modifying the software code running thereon, is selectively configurable to change its set of available features and/or change the way in which a given feature(s) behaves; some of these features may be selectively programmable by the user.

The apparatus 100 further includes an interface 112, which may be wired and/or wireless, in operative communication with the controller 110. In one or more embodiments, the interface 112 is wireless and is therefore coupled with an antenna 114 for transmitting signals from the controller 110 and/or for receiving signals to be presented to the controller for subsequent processing. The interface 112 is preferably configured to convert signals received from the controller 110 into a format suitable for transmission by the antenna 114, and similarly to convert signals received by the antenna into a format suitable for use by the controller. The interface 112 may employ essentially any communications protocol(s) as will be known by those skilled in the art, such as, but not limited to, Universal Serial Bus (USB) and Ethernet, in the case of a wired interface, and Bluetooth, Bluetooth Low Energy (BLE), Wi-Fi (based on IEEE 802.11 standards), ZigBee (based on IEEE 802.15.4 standard) and infrared/optical, in the case of a wireless interface.

A display driver 116 included in the apparatus 100 in operative communication with the controller 110 is preferably configured to receive an output signal generated by the controller that is intended for presentation to the user and to covert this signal into a form suitable for graphical presentation on a display 118 of the apparatus. At a high level, the display driver 116 interfaces between the controller 110 and the display 118. In one or more embodiments, the display driver functionalities, or at least a portion thereof, may be integrated into the display 118, thereby eliminating the need for a separate display driver. The display 118, which may be implemented using, for example, a small (e.g., about 1.5-2 inches, the size of a smart watch display) liquid crystal display (LCD) or organic light-emitting diode (OLED) display, provides a visual indication to the user of data, graphics and warnings, as well as other information that may be desirable. The size and/or resolution (e.g., pixel count) of the display 118, as well as other characteristics of the display (e.g., color), is preferably selected to be appropriate for clearly and accurately presenting to the user information from the controller 110, including, but not limited to, percentage of blood oxygen saturation level, hypoxia alerts, heart rate, altitude, time, date, etc. Optionally, the display 118 may be touch sensitive, allowing the user to scroll and select menu options and enter information by touching a selected point or region on the display.

In one or more embodiments, a backlight color of the display 118 is changeable in response to a signal(s) from the controller 110, as previously stated. In this manner, the controller 110 can advantageously alert the user to his or her hypoxia status in a passive manner; that is, without any action or input required by the user. For instance, in a preferred embodiment, the controller 110 is configured to assign a measured blood oxygen saturation level of the user into one of three or more different categories indicative of a status of potential risk of hypoxia, and thus bodily function impairment. In a first assigned category, which may represent a measured blood oxygen saturation level in a normal range of about 93%-100%, the controller 110 may send a signal to the display 118 causing a backlight color of the display to be a first color, preferably green, indicating normal blood oxygen saturation levels. When the measured blood oxygen saturation level of the user falls into a warning range of about 80%-92%, the controller 110 may send a signal to the display 118 causing the backlight color of the display to change to a second color, preferably yellow or orange, indicating an onset of hypoxia. This allows the user to take appropriate corrective action, such as, for example, using supplemental oxygen or physically moving to a lower altitude. At this warning stage, the controller 110 may be configured to engage other methods of alerting the user, including the activation of audible and/or tactile devices (e.g., a pulsing alarm). When the measured blood oxygen saturation level of the user drops below the warning range and into a critical range of less than about 80%, the controller 110 may send a signal to the display 118 causing the backlight color of the display to change to a third color, preferably red, indicating a state of severe hypoxia. Additionally, at this critical stage, the controller 110 may be configured to modify the type of audible and/or tactile alarms (e.g., changing from a pulsing alarm to a constant alarm).

It is to be appreciated that the specific colors and corresponding assigned ranges of blood oxygen saturation percentage are not limited by embodiments of the invention, nor is the number of different colors limited to three. Rather, embodiments of the invention similarly contemplate the use of less than three colors (e.g., two) or more than three colors (e.g., four) of display backlighting. Using more display backlighting colors and corresponding assigned ranges of blood oxygen saturation levels provides a finer degree of hypoxia status indication to the user.

As stated above, the apparatus 100, in one or more embodiments, is beneficially configured to provide audible and/or tactile feedback to the user, in addition to visual notifications. Specifically, the apparatus 100 optionally comprises an audio driver 120 and an audible indicator 122 coupled with the audio driver. The audio driver 120 is in operative communication with the controller 110 and is adapted to receive a signal generated by the controller that is intended for audible presentation, such as, for example, an alarm signal, and to convert such signal to an appropriate form suitable for use by the audible indicator 122. At a high level, the audio driver 120 interfaces between the controller 110 and the audible indicator 122. By way of illustration only, the audible indicator 122 may comprise a speaker and the controller 110 may generate a digital output signal (e.g., an enable signal) when the oximeter sensor 102 indicates that the user's measured blood oxygen saturation level has dropped below a prescribed normal threshold (e.g., less than about 92%). The audio driver 120 may include an oscillator which, upon receipt of this output signal from the controller 110, is configured to generate a sinusoidal audio output signal (e.g., about 500-1,000 hertz) of an appropriate level to drive the audible indicator/speaker 122. In one or more embodiments, the controller 110 is configured to cause the audible indicator 122 to generate a continuous sequence of intermittent (i.e., periodic) alert tones or bursts of tones when an onset of hypoxia is detected (to thereby serve as a warning), based on measured blood oxygen saturation level of the user, and is configured to cause the audible indicator to generate a constant alert tone, or at least a tone that is different than the warning tone indicating the onset of hypoxia, when severe hypoxia is detected.

Similarly, the apparatus 100 may optionally include a tactile driver 124 and a tactile device 126 coupled with the tactile driver. The tactile driver 124 is in operative communication with the controller 110 and is adapted to receive a signal generated by the controller that is intended for tactile presentation, such as, for example, an alarm signal, and to convert such signal to an appropriate form suitable for use by the tactile device 126. At a high level, the tactile driver 124 interfaces between the controller 110 and the tactile device 126. By way of illustration only, the tactile device 126 may comprise a piezoelectric element and the controller 110 may generate a digital output signal (e.g., enable signal) when the oximeter sensor 102 indicates that the user's blood oxygen saturation level has dropped below a prescribed normal threshold (e.g., less than about 92%). The tactile driver 124 may include an oscillator which, upon receipt of this output signal from the controller 110, is configured to generate an output signal of an appropriate level to drive the tactile/piezoelectric device 126 so as to cause the tactile device to vibrate and thereby alert the user to the alarm condition. In one or more embodiments, the controller 110 is configured to cause the tactile device 126 to vibrate intermittently (i.e., periodically, such as pulsed) when an onset of hypoxia is detected based on measured blood oxygen saturation level of the user, and is configured to cause the tactile device to vibrate continuously when severe hypoxia is detected.

In one or more embodiments, the apparatus 100 optionally includes a position engine or module 128 in operative communication with the controller 110. The position engine 128 may include a global positioning system (GPS) module, altimeter, or the like, adapted to obtain location information, including altitude and/or terrestrial coordinates, and to present such location information to the controller 110 for further processing. In one or more embodiments, the controller 110 uses this location information, particularly altitude, in monitoring the hypoxic state of the user. As previously stated, altitude can significantly influence the onset of hypoxia and/or the susceptibility to hypoxia in a person, primarily because the amount of available oxygen in the ambient air decreases with increasing height above sea level. Altitude/location information obtained from the position engine 128 may be sent by the controller 110 for presentation to the user on the display 118 (e.g., in the form of an altitude reading (height above sea level), longitude and latitude coordinates, GPS coordinates, physical address, etc.).

In some embodiments, memory 130, coupled with and/or included in the controller 110, may be used to store historical data relating to environmental conditions (e.g., altitude, position, etc.) and/or physiological factors of the user (e.g., blood oxygen saturation levels, heart rate, etc.). The controller 110 is preferably configured to display one or more of these environmental conditions and/or physiological factors as a function of time on the display 118, such as by way of a line graph or other visual presentation format as will become apparent to those skilled in the art given the teachings herein. For example, in one or more embodiments, the controller 110 may generate appropriate signals which cause the display 118 of the apparatus 100 to present a graphical plot of historical blood oxygen saturation levels and/or altitude as a function of time; real-time blood oxygen saturation levels and/or altitude may be similarly plotted on the display. In some embodiments, the controller 110 is configured to transfer, through a wired and/or wireless communication channel, at least a portion of the stored historical environmental and/or physiological data relating to the user to another system, such as, but not limited to, a plane's black box recording device, a pilot's electronic flight bag, a portable computing device (e.g., iPad), a smart phone, etc.

The user may, optionally, select what information is to appear on the display 118 or the manner in which the information is presented (e.g., position on the display, units, size, font, etc.). In other embodiments, the memory may be external to the apparatus 100 and in operative communication with the controller 110, such as via the interface 112. In this manner, historical data may be stored by the user on a removal memory card, flash drive, or the like. In some embodiments, the memory 130 may also be used to store one or more user preferences affecting operation of the hypoxia monitoring apparatus 100.

Figure 2:
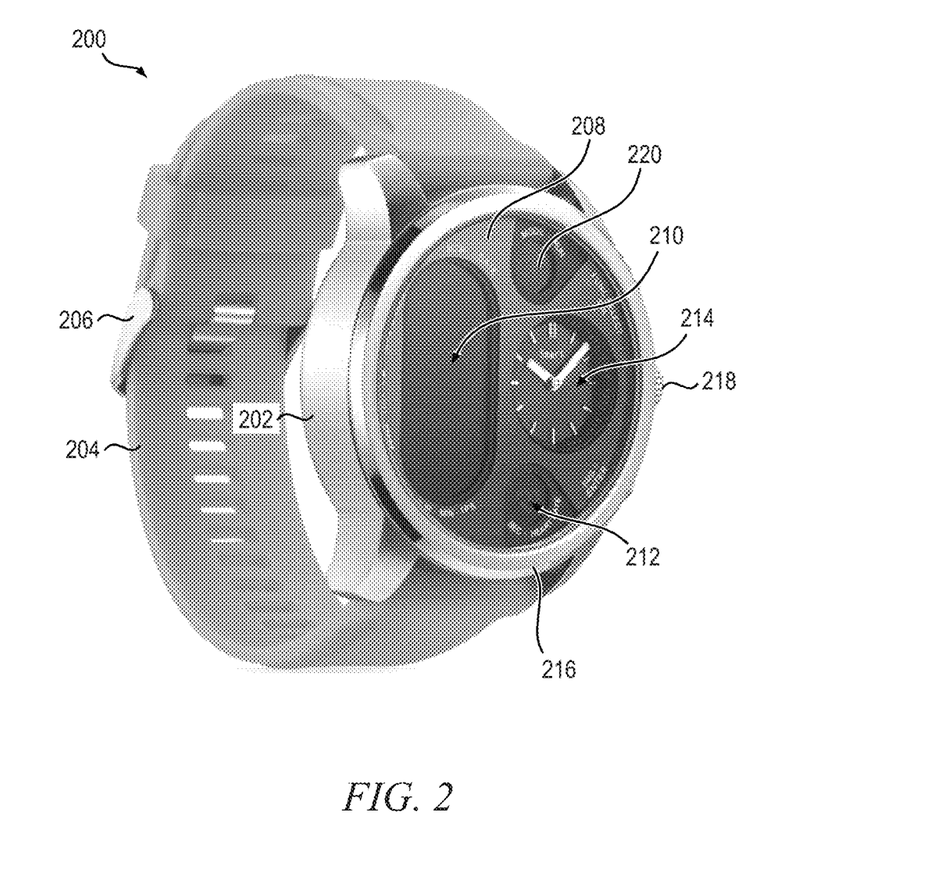
FIG. 2 is a perspective view depicting at least a portion of an illustrative wrist-worn oximeter device incorporating the exemplary hypoxia monitoring apparatus shown in FIG. 1, according to an embodiment of the present invention.

FIG. 2 is a perspective view depicting at least a portion of an illustrative wrist-worn oximeter device 200 incorporating the exemplary hypoxia monitoring apparatus 100 shown in FIG. 1, according to an embodiment of the invention. With reference to FIG. 2, the illustrative oximeter device 200 is shown in the form of a smart watch or other wrist-worn computing device, although alternative manifestations of the device are similarly contemplated and within the scope of the invention. In this example, the oximeter device 200 includes a main body 202 affixed to an attachment means for removably attaching the device to the wrist of a user. In one or more embodiments, the attachment means comprises a wrist strap 204 and a fastener 206, which may be a buckle, although other types of fasteners are similarly contemplated, such as, but not limited to, a snap, Velcro, etc. The wrist strap 204 is preferably formed in two pieces which are joined together by the fastener 206, as will be known by those skilled in the art. The wrist strap 204 and fastener 206, working in conjunction with one another, are adapted to allow the user to adjust a diameter of the attachment means to accommodate the size of the user's wrist. In an alternative embodiment, the wrist strap 204 may be formed as a continuous band which is elastic (e.g., rubber) or is otherwise capable of stretching to accommodate different size wrists, thereby eliminating the need for a separate fastener 206.

For accurate measurement and monitoring of blood oxygen saturation levels, the oximeter sensor (e.g., 102 in FIG. 1) of the device 200 is preferably disposed in contact with the skin so that light transmitted by the sensor passes through the bloodstream of the user and the light which is not absorbed by hemoglobin in the blood is detected by the light detector in the sensor, as previously described. Hence, the device 200 should be affixed to the wrist of the user in a manner which prevents significant movement of the device.

The main body 202, in this exemplary embodiment, is cylindrical in shape (e.g., in the form of a smart watch) and is adapted to contain the functional circuitry of the hypoxia monitoring apparatus 100 shown in FIG. 1. It is to be understood, however, that the specific shape and/or dimensions of the main body 202 are not limited by embodiments of the invention. For example, the main body may, in one or more embodiments, be rectangular in shape. More particularly, the main body 202 is preferably formed of a substantially rigid material (e.g., metal, plastic, etc.) having an interior space adapted to contain at least a portion of the circuitry of the hypoxia monitoring apparatus 100 (FIG. 1), including a battery (e.g., button cell battery) or other portable power source. The main body 202 may include a removable panel or the like through which the user can replace the battery when depleted. In other embodiments, the battery may be rechargeable, either via a wired connection port in the main body 202 or wirelessly (e.g., magnetic induction charging).

The main body 202 also preferably contains an antenna (114 in FIG. 1) for embodiments of the apparatus 100 comprising a wireless interface (112 in FIG. 1). In some embodiments, the antenna may be integrated into the main body 202 itself (e.g., as part of the body case/housing), where at least a portion of the body is formed of conductive material. Alternatively, a connection or port (not explicitly shown, but implied) may be provided in the main body for coupling an external antenna to the device 200.

The oximeter device 200 includes a front faceplate 208 having one or more openings, 210, 212 and 214, through which portions of the display (e.g., 118 in FIG. 1) of the hypoxia monitoring apparatus, among other features of the device, can be viewed by the user. The faceplate 208 may optionally be protected by a clear cover (not explicitly shown, but implied), and the faceplate and cover held in place by attachment to the main body 202 using a bezel 216 or other attachment arrangement. A main region of the display, which may present critical information, such as, for example, current blood oxygen saturation level, altitude, alerts, etc., is preferably viewed through a first (larger) opening 210, while other pertinent information (e.g., heart rate) is viewed through a second (smaller) opening 212. The device 200 may include an analog clock movement which is viewed through a third opening 214. Time and/or date adjustment may be accomplished using an adjustment control 218 in a standard manner.

It is to be appreciated that although an analog timepiece is shown in the oximeter device 200, time and/or date functionality may, alternatively, be optionally presented on the display 118 (FIG. 1), either in a simulated analog or a digital format, and viewed through the opening 214 in the faceplate 208. Moreover, the adjustment control 218 may be used to control other features of the device 200, such as, for example, setting a mode of operation of the device, setting and cancelling alarms, turning on device backlighting for nighttime use, etc., as will become apparent to those skilled in the art given the teachings herein. In this manner, the same adjustment control 218 can be used to control more than one function of the oximeter device 200.

Although not explicitly visible in FIG. 2, the oximeter device 200 includes an oximeter sensor accessible through a bottom and/or sides of the main body 202, and/or mounted to the wrist strap 204. Furthermore, in embodiments in which an audible indicator (122 in FIG. 1) is employed, the audible indicator may be mounted to the main body 202, and openings in the sides and/or bottom of the device 200 may be included through which sound can pass. In embodiments in which a tactile device (126 in FIG. 1) is employed, the tactile device can be mounted to the main body 202 (e.g., on a bottom surface of an interior of the main body) with or without openings. The tactile device, when activated, will cause a vibration of the main body 202 that will be felt by the user when the oximeter device 200 is affixed to the user's wrist to thereby alert the user to a prescribed condition without the need for the user to view the display of the oximeter device or listen to audible indicator.

Optionally, in one or more embodiments, the oximeter device 200 includes a front facing camera 220, accessible through one of the openings in the faceplate 208, and a microphone. The camera 220 and microphone provide the user with the ability to engage in video communications (e.g., video chatting, FaceTime, Skype, etc.). In some embodiments, the camera 220 and/or microphone may be used to gauge a responsiveness of the user; for example, to determine whether the user is awake or speaking coherently. Visual and/or audible information can be beneficially employed to supplement other physiological factors obtained by the controller (110 in FIG. 1) in determining the stage of hypoxia in the user.

Figure 3:
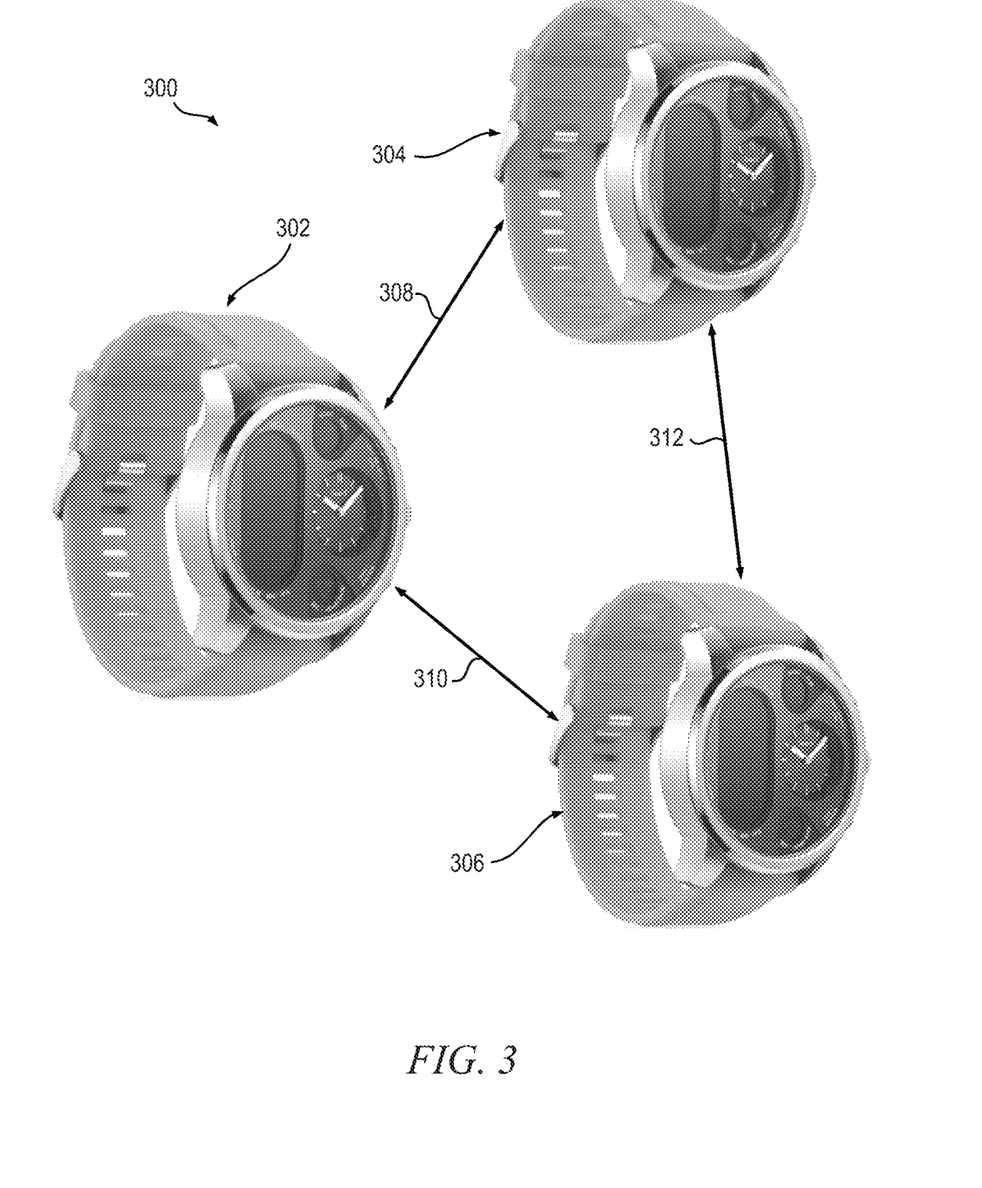
FIG. 3 is a conceptual view depicting at least a portion of an exemplary network including multiple oximeter devices operating in a group protection mode, according to an embodiment of the present invention.

In one or more embodiments, the hypoxia monitoring apparatus (100 in FIG. 1) is capable of operating in a "group protection" mode. This feature is particularly beneficial for applications in which there are group of individuals (2 or more) in close relative proximity to one another, for example, when flying a plane in which there is a pilot and at least one co-pilot, or when there is a group of mountain climbers. By way of example only and without limitation, FIG. 3 is a conceptual view depicting at least a portion of an exemplary network 300 including multiple interconnected oximeter devices operating in a group protection mode, according to an embodiment of the invention. As apparent from FIG. 3, a plurality of oximeter devices, 302, 304 and 306, formed according to embodiments of the invention, are preferably in operative communication with one another. Specifically, a first oximeter device 302 and a second oximeter device 304 are configured to communicate with one another using a first communication channel 308 established therebetween. Likewise, the first oximeter device 302 and a third oximeter device 306 are configured to communicate with one another using a second communication channel 310 established therebetween, and the second oximeter device 304 and third oximeter device 306 are configured to communicate with one another using a third communication channel 312 established therebetween.

The various communication channels 308, 310, 312 may be wired or wireless, and all communications channels need not be of the same type. For example, the first communication channel 308 may be a wired USB connection, and the second communication channel 310 may be a wireless connection using a known wireless communication protocol (e.g., Bluetooth or Wi-Fi). In one illustrative embodiment, the oximeter devices 302, 304, 306 are configured to communicate with one another wirelessly using a Bluetooth communication protocol as part of an ad hoc local area network (LAN) or other small area network. An ad hoc network is a network with temporary plug-in connections, in which the network devices 302, 304, 306 are part of the network only for the duration of a communications session or, in the case of mobile or portable devices, while in close proximity (e.g., about 30 feet) to the rest of the network. It is to be appreciated that embodiments of the invention are not limited to any specific number of interconnected devices.

The group protection mode feature of the oximeter device beneficially facilitates a group or team of users, interconnected through their respective oximeter devices, to monitor each other and to be alerted when a group member whose blood oxygen saturation level, or another monitored physiological condition (e.g., heart rate, etc.), poses a danger to the person's consciousness, bodily functioning, or general well-being. More particularly, in the group protection mode, a given one of the oximeter devices (e.g., 302) is preferably configured to send an alert notification to at least a subset of the other oximeter devices in the network (e.g., 304, 306), so that at least one of the other members in the group will be made aware of a possible physiological impairment occurring in a given one of the members in the group. This is advantageous especially when the group member becomes unconscious or is otherwise unresponsive to an alert from the member's monitoring device indicating the onset of hypoxia or the presence of acute hypoxia, or some other physiological impairment.

In one or more embodiments, an alert notification sent by a given group member's oximeter device is broadcast to the other group members in the network and presented on a portion of the displays of the group members' respective oximeter devices. The alert notification is preferably displayed along with information identifying which one of the interconnected group members is experiencing the impaired physiological condition. In this regard, the alert information is received by the wireless interface (112 in FIG. 1) in each of the interconnected oximeter devices in the network and is sent to the controller (110 in FIG. 1) of each device for further processing and display of the alert condition to the users. When the alert is of a more serious nature, the audible and/or tactile devices in the respective interconnected oximeter devices of the group members are activated to provide the users with an enhanced notification mechanism.

In an illustrative group protection scenario, a first oximeter device 302 associated with a first group member/user determines that the blood oxygen saturation level of the first group member has fallen below a prescribed threshold (e.g., in a range of about 80%-92%). In response, the controller (110 in FIG. 1) in the first oximeter device 302 causes the display backlighting of the first oximeter device to change from green to yellow. The controller in the first oximeter device 302, being operative in a group protection mode, transmits an alert through the wireless interface (112 in FIG. 1) in the device (e.g., using a Bluetooth or Wi-Fi communication protocol), to the second and third oximeter devices, 304 and 306, respectively. The respective wireless interfaces in the second and third oximeter devices 304, 306 receive the alert signal transmitted by the first oximeter device 302 and the information is sent to the controllers for further processing. The respective controllers present this information to the displays of the second and third oximeter devices 304, 306 to alert second and third group members/users associated with the second and third oximeter devices that the first group member is experiencing an onset of hypoxia, whereby corrective action can be taken by the second and/or third group member to assist the first group member, should the first group member be non-responsive to the alert. In this manner, embodiments of the invention provide redundant hypoxia monitoring of all group members, which is an advantageous backup safety feature.

Figure 4:
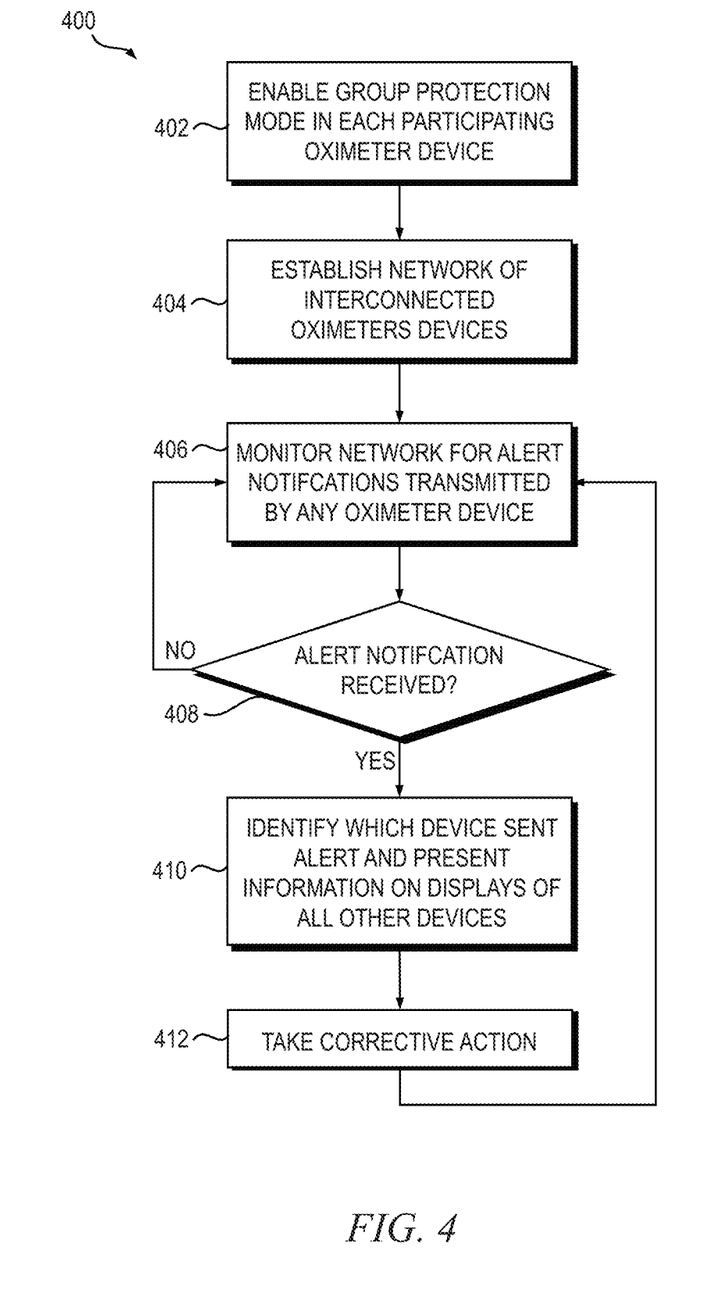
FIG. 4 is a flow diagram depicting at least a portion of an exemplary group protection method that may be performed by oximeters devices in a group of participating users, according to an embodiment of the present invention.

FIG. 4 is a flow diagram depicting at least a portion of an exemplary group protection method 400 that may be performed by a plurality of oximeters devices in a group of participating users, according to an embodiment of the invention. With reference to FIG. 4, the method 400 includes enabling the group protection mode on all participating oximeter devices in a group of users in step 402. This mode may be enabled, for example, by a user entering a selection on his or her oximeter device. Once two or more oximeter devices are enabled for group protection, step 404 attempts to establish a network of interconnected devices. The protocol for establishing the network will depend, at least in part, on the communication protocol used by the devices. For example, using a Bluetooth protocol, an ad hoc network can be established by causing each of the devices to enter a discovery mode, wherein a prescribed handshaking procedure is activated to establish a connection between devices, as will be known by those skilled in the art.

With the network of interconnected devices established in step 404, each of the devices in the network monitors the other devices for transmission of an alert notification in step 406. In step 408, the controller in each device checks to see whether an alert notification has been received. If no alert notification has been received, the method 400 continues to step 406 where the devices resume monitoring the network for alert notifications from any oximeter device. If an alert notification has been received in step 408, the identity of the oximeter device which sent the alert notification is obtained and this information is presented on the displays of all interconnected oximeter devices in the network in step 410. In step 412, corrective action is taken by one or more group members to prevent the user whose device issued the alert notification from becoming hypoxic.

At least a portion of the apparatus of the present invention may be implemented in an integrated circuit. In forming integrated circuits, identical die are typically fabricated in a repeated pattern on a surface of a semiconductor wafer. Each die includes a device described herein (e.g., piezoelectric element, tuning inductor, etc.), and may include other structures and/or circuits. The individual die are cut or diced from the wafer, then packaged as an integrated circuit. One skilled in the art would know how to dice wafers and package die to produce integrated circuits. The exemplary apparatus illustrated in the accompanying figures, or portions thereof, may be part of an integrated circuit. Integrated circuits so manufactured are considered part of this invention.

An integrated circuit in accordance with aspects of the present disclosure can be employed in essentially any application and/or system where non-invasive monitoring of hypoxia (e.g., measurement of blood oxygen saturation) is desired. Systems incorporating such integrated circuits are considered part of this invention. Given the teachings of the present disclosure provided herein, one of ordinary skill in the art will be able to contemplate other implementations and applications of embodiments of the invention.

The methodologies of embodiments of the present disclosure may be particularly well suited for use in a wearable electronic device or alternative system. Accordingly, embodiments of the present disclosure may take the form of an entirely hardware embodiment or an embodiment combining software and hardware aspects that may all generally be referred to herein as a "controller," "processor," "circuit," "module" or "system." Furthermore, embodiments of the present disclosure, or portions thereof, may take the form of a computer program product embodied in one or more non-transitory computer readable medium(s) having computer readable program code stored thereon.

Any combination of one or more non-transitory computer-usable or computer-readable medium(s) may be utilized. The computer-usable or computer-readable medium may be a computer-readable storage medium. A computer-readable storage medium may be, for example but not limited to, an electronic, magnetic, optical, electromagnetic, infrared, or semiconductor system, apparatus, device, or any suitable combination of the foregoing. More specific examples (a non-exhaustive list) of the computer-readable storage medium would include the following: a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the context of this disclosure, a computer-readable storage medium may be any tangible, non-transitory medium that can contain or store a program for use by or in connection with an instruction execution system, apparatus or device.

Computer program code for carrying out operations of embodiments of the present disclosure may be written in any combination of one or more programming languages, including an object oriented programming language such as Java, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments of the present disclosure are described herein with reference to a block diagram of apparatus (systems). It will be understood that each functional block of the block diagram (e.g., FIG. 1), and combinations of blocks in the block diagram, may be implemented at least in part by computer program instructions. These computer program instructions may be stored in a computer-readable medium that can direct a computer or other programmable data processing apparatus or processor to function in a particular manner, such that the instructions stored in the computer-readable medium produce an article of manufacture including instruction means which implement the function/act specified in the block diagram block or blocks.

The illustrations of embodiments of the present invention described herein are intended to provide a general understanding of the various embodiments, and are not intended to serve as a complete description of all the elements and features of apparatus and systems that might make use of the circuits and techniques described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not necessarily drawn to scale. Accordingly, the specification and drawings are to be regarded in an illustrative rather than a restrictive sense.

Embodiments of the invention are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "upper," "lower," "front" and "back," where used, indicate relative positioning of elements or structures to each other when such elements are oriented in a particular manner, as opposed to defining absolute positioning of the elements.

The corresponding structures, materials, acts, and equivalents of all means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, inventive subject matter lies in less than all features of a single embodiment. Thus the following claims are hereby incorporated into the Detailed Description, with each claim standing on its own as separately claimed subject matter.

Given the teachings of embodiments of the invention provided herein, one of ordinary skill in the art will be able to contemplate other implementations and applications of the techniques of embodiments of the invention. Although illustrative embodiments of the invention have been described herein with reference to the accompanying drawings, it is to be understood that embodiments of the invention are not limited to those precise embodiments, and that various other changes and modifications are made therein by one skilled in the art without departing from the scope of the invention, as manifested in the accompanying claims.

What is claimed is:

1. An oximetry device for monitoring blood oxygen saturation of a user, the oximetry device comprising:
    a main body;
    a wrist strap coupled with the main body and adapted to removably secure the main body on a wrist of the user during operation of the device; and
    an interface in operative communication with a controller;
    wherein the main body includes an oximeter sensor adapted to generate an output signal indicative of measured blood oxygen saturation, the controller in operative communication with the oximeter sensor and configured to determine a percentage blood oxygen saturation of the user as a function of the output signal generated by the oximeter sensor, and a display for presenting visual information generated by the controller to the user;
    wherein the oximetry device is a first oximetry device configured to operate in a group protection mode, and wherein the interface comprises a wireless interface configured to communicate, using a wireless communication protocol, with at least a second oximetry device also configured to operate in a group protection mode to establish a network therebetween, the first oximetry device wirelessly transmitting an alert signal to the second oximetry device when the blood oxygen saturation of the user of the first oximetry device falls below a prescribed threshold level, a controller in the second oximetry device operating in the group protection mode being configured to receive the alert signal and to present an alert indication to a user of the second oximetry device; and
    wherein the controller in the first oximetry device operating in the group protection mode is configured to wirelessly receive an alert signal from the second oximetry device when the blood oxygen saturation of the user of the second oximetry device falls below a prescribed threshold level and to present an alert indication to the user of the first oximetry device.

2. The oximetry device according to claim 1, wherein the main body further comprises a position module in operative communication with the controller in the first oximetry device and configured to obtain location information relating to the oximetry device, the location information including at least one of terrestrial coordinates and altitude.

3. The oximetry device of claim 2, wherein the controller in the first oximetry device is configured to determine a state of hypoxia of the user of the first oximetry device as a function of the measured blood oxygen saturation and the location information of the user of the first oximetry device.

4. The oximetry device of claim 2, wherein position module comprises at least one of a global positioning system (GPS) module and an altimeter.

5. The oximetry device of claim 1, wherein the controller in the first oximetry device is configured to present an alert indication to the user of the first oximetry device when the blood oxygen saturation of the user falls below a prescribed threshold level.

6. The oximetry device of claim 5, wherein the alert indication comprises at least one of a visual indication, an audible indication and a tactile indication.

7. The oximetry device of claim 1, wherein the controller in the first oximetry device is configured: to set the display backlighting to a first color when the measured blood oxygen saturation level of the user of the first oximetry device is within a first range; to set the display backlighting to a second color when the measured blood oxygen saturation level of the user of the first oximetry device is within a second range; and to set the display backlighting to a third color when the measured blood oxygen saturation level of the user of the first oximetry device is within a third range.

8. The oximetry device of claim 7, wherein the first color is green, the second color is orange and the third color is red, and wherein the first range is greater than 92 percent to 100 percent, the second range is 80 percent to 92 percent, and the third range is less than 80 percent.

9. The oximetry device of claim 7, wherein the first oximetry device comprises a tactile driver and a tactile device coupled with the tactile driver, and wherein the controller in the first oximetry device is configured to generate an output signal that causes the tactile device to vibrate intermittently when the measured blood oxygen saturation level of the user of the first oximetry device is within the second range, and to cause the device to vibrate continuously when the measured blood oxygen saturation level of the user of the first oximetry device is within the third range.

10. The oximetry device of claim 7, wherein the first oximetry device comprises a tactile driver and a tactile device coupled with the tactile driver, and wherein the controller in the first oximetry device is configured to generate an output signal supplied to the tactile driver that causes the tactile device to emit an intermittent audible alert when the measured blood oxygen saturation level of the user of the first oximetry device is within the second range, and to cause the tactile device to emit a continuous audible alert when the measured blood oxygen saturation level of the user of the first oximetry device is within the third range.

11. The oximetry device of claim 1, wherein the main body further comprises memory in operative communication with the controller in the first oximetry device, the memory storing at least one of historical physiological information of the user of the first oximetry device, historical environmental information, and one or more user preferences affecting an operation of the device.

12. The oximetry device of claim 1, wherein the main body further comprises signal conditioning circuitry configured to at least one of amplify a voltage level of an output signal generated by the oximeter sensor and to remove noise components present in the output signal generated by the oximeter sensor.

13. The oximetry device of claim 1, wherein the display comprises a changeable backlighting color, and wherein the controller in the first oximetry device is configured to adjust a color of the display backlighting as a function of a measured blood oxygen saturation of the user of the first oximetry device.

14. The oximetry device of claim 1, wherein the first oximetry device is configured to communicate with a plurality of other oximetry devices in the network, and wherein an alert signal transmitted by a given one of the oximetry devices in the network causes an alert indication to be presented on a display of each of at least a subset of the other oximetry devices in the network along with information identifying which of the oximetry devices in the network transmitted the alert signal.

* * * * *